United States Patent
James

(10) Patent No.: US 6,328,760 B1
(45) Date of Patent: Dec. 11, 2001

(54) PULSED PLASMA RADIATION DEVICE FOR EMITTING LIGHT IN BIOLOGICALLY SIGNIFICANT SPECTRAL BANDS

(76) Inventor: Robert G. James, 2713 Vyn Dr., Bakersfield, CA (US) 93306

( * ) Notice: Subject to any disclaimer, the term of this patent is extended or adjusted under 35 U.S.C. 154(b) by 0 days.

(21) Appl. No.: 09/467,124

(22) Filed: Dec. 20, 1999

(51) Int. Cl.[7] .................................................. A61N 5/006
(52) U.S. Cl. .............................. 607/88; 607/90; 607/91; 607/96; 606/9; 606/10; 606/13; 422/186.23
(58) Field of Search .................................. 607/88–91, 93, 607/94, 96; 606/9, 10, 13; 315/5, 111.2–111.41; 310/11; 204/164, 168; 422/186.21, 186.23

(56) References Cited

U.S. PATENT DOCUMENTS

| | | | |
|---|---|---|---|
| 4,249,537 | * | 2/1981 | Lee et al. ............................. 128/422 |
| 4,430,999 | * | 2/1984 | Brighton et al. ...................... 128/419 |
| 5,217,009 | * | 6/1993 | Kronberg ............................. 128/419 |

* cited by examiner

Primary Examiner—Linda C. M. Dvorak
Assistant Examiner—A. Farah
(74) Attorney, Agent, or Firm—George A. Bode; Bode & Associates

(57) ABSTRACT

A plasma tube is provided in which water vapor, carbon dioxide, molecular nitrogen and a simple hydrocarbon are excited to ionization to emit electromagnetic frequency spectra for exciting electron orbitals of biological tissue. The anode end of the tube is shielded by a cylindrical shield electrically connected to the anode, while a reflector and a transversely polarized magnetic piece direct the spectral emissions adjacent the cathode towards the skin of a person. The tube is pulsed to ionization in a pulse waveform that comprises the frequency domain of biological electrochemistry. In this manner the molecular architecture of a cell is excited to promote the cell growth process.

6 Claims, 3 Drawing Sheets

PULSED PLASMA RADIATION DEVICE FOR EMITTING LIGHT IN BIOLOGICALLY SIGNIFICANT SPECTRAL BANDS

BACKGROUND OF THE INVENTION

1. Field of the Invention

The present invention relates to pulsed plasma devices, and more particularly to plasma tubes conformed to ionize gases in the organic protein group.

2. Description of the Prior Art

In the course of evolution the smallest biological system, a living cell, has evolved polarized membranes which act both as capacitors and ionic pumps for maintaining the potentials and current flows of a wet electrical circuit. Thus, for example, the cell membrane's selective permeability of potassium (K) and sodium (Na) results in a potential difference known as the Na+/K+ pump, or electromotive force which transports selected ions across the membrane to maintain a balance. This tightly controlled balance in its various specialized forms is fundamental to life. For example in neurons the cell wall potential acts as a voltage gated Na+ pump to transmit nerve signals in response to external stimuli, in cell growth as a mechanism for transporting food (selected elements) into the cell interior, and so on.

Electrical potential, moreover, is intimately involved in virtually all cell functions. The piezoelectric signals of a bone under strain has been widely recognised as a mechanism for promoting its growth. At the microscopic level this effect is obtained by strain distortions of some of the long-chain molecules like collagen, elastin or keratin, exhibiting piezoelectric potential changes when stretched, which changes then promote growth of the ligament juncture, sectional growth and other tissue changes.

the electrical nature of all biological processes is therefore well established and has been used to advantage in various therapeautic mechanisms like that described in U.S. Pat. No. 4,430,999 to Brighton, et al, for promoting osteogenesis; U.S. Pat. No. 5,217,009 to Kronberg for stimulating bone tissue by electrical pulses; and others. Similarly, the 'wet circuit' analogy of a cell is also well established, e.g., Alberts, et al, MOLECULAR BIOLOGY OF THE CELL, 2nd Ed, 1989, Garland Publishing, Inc., New York., N.Y.

The ionic nature of the cell interacts with various dipoles, i.e., molecules that are electrically neutral but carry charges at their ends. These then interact with the weakly polar structure of water, thereby effecting the 'wet' circuit. This electrical system of the living cell, therefore, must be included in all models of cell biology.

The electrical potential, in turn, depends on the excitation state of the electrons. It is well known that when the electron around any element is at its base or ground state its ionization potential is at its greatest. The electron orbital state, therefore, affects the ionization potential and consequently the dissociation of the various molecular bonds is dependent on the electron excitation state. The characteristic discrete absorption-emission bands of each element then define, in electromagnetic energy, the difference in potential between the lowest and higher electron states.

the same exchange between discrete frequency spectra and electron orbital state is also useful as a mechanism to promote chemical reactions. Thus, for example, some biological processes entailing melanin are promoted in the presence of ultraviolet light, various resin reactions are advanced by light of a particular frequency and numerous other reactions are associated with light. The utility of specific frequency light to promote a particular reaction is therefore well established.

At the cell level inherent in any 'wet' circuit is the notion of a characteristic frequency that is relatively quite low. For example, the ionic exchange at the cell wall is at the low electro-chemical frequency which, at its fastest, is associated with the nerve signal propagation across neurons, and similar time constants are associated with Negro-muscular response, mental processing interval and other characteristic frequencies of a biological structure. Typically the frequency band of these responses is constrained by scale, where the so-called scaling laws limit the dynamic response to the confines of the structure. simply, an organism cannot move so fast as to rip itself apart.

By scale, this biological frequency domain is wholly separated from the electromagnetic frequencies associated with the electron orbitals. Accordingly, a certain amount of 'immunity' to various light spectra is inherent in a biological structure, allowing for a functioning system in all sorts of backgrounds. This same immunity, however, limits the efficacy of any synthetic repair or alteration process.

It is believed that for the foregoing reasons the prior art mechanisms have had less than an optimal result in affecting biological changes. To obtain the most effective results signals in both of these disparate frequency domains need to be issued, the first to promote the reactivity of the elements and the second to direct the reaction to a form consistent with cell biology. It is this wide spread in frequency domains that has not been heretofore effectively accomodated. A system that effectively operates in both frequency ranges is therefore desired and it is one implementation of such system that is disclosed herein.

SUMMARY OF THE INVENTION

Accordingly, it is the general purpose and object of the present invention to provide a pulsed plasma tube system in which gases in the organic element group are cyclically ionized to illuminate biological surfaces.

Other objects of the invention are to provide a pulsed plsma tube conformed to emit light frequencies in the biological element group.

Yet further objects of the invention are to provide a plasma discharge device useful to rejuvenate skin surfaces.

Further objects of the invention are to provide a pulsed plasma device conformed to discharge at pulse rates in the frequency domain of a wet biological circuit.

Briefly these and other objects are accomplished within the present invention by way of a plasma tube connected in a voltage multiplier circuit that is cyclically operated by an oscillator. The plasma tube includes a cathode and an anode aligned along a discharge axis adjacent a magnet in order to help direct the ionized flows together with the attractive aspects of a foil or sheet configuration of the cathode lead to be then reflected. In this form a high discharge area is developed within the tube for illuminating biological surfaces.

Those skilled in the art will appreciate that the gas discharge within the tube will be associated with emission of light at the distinct frequencies that characterise the gas elements within the tube. Accordingly, the high discharge area of the tube will radiate onto adjacent surfaces the discrete frequencies that are associated with ionization of the gases in the tube. By filling the tube with gases in the following ratio grouping:

H2O=66%
CO2=24%
N2=3%
H2CO3=3% discharge frequency spectra are generated which are consistent with the absorption spectra of biological matter. The tube, therefore, becomes useful to promote chemical reactions in the illuminated biological structure, which occur at the characteristic frequencies of the 'wet' circuit that defines the cell biology. The pulsing of the discharge in these frequency domains then further enhances the efficacy of the process.

Those in the art will appreciate that the structure of biological matter, such as protein, contains about 96% of its weight in the elements O, C, H and N. The spectral absorption bands of these elements, in their several molecular combinations, will therefore coincide with the plasma emissions of the above gas group. Moreover, a typical protein includes polar, non-polar, semi-polar and ionizable portions or side chains which respond in specific manners to electrical charge, and to selected spectra as well. In this setting the H2O, CO2 and N2 portions of the plasma provide the radiation matrix or background radiation level on top of which the H2CO3 (carbonic acid) emission spectra are passed. This then emits on top of the raised background level the spectral signature of the most basic building block of a carbohydrate chain to interact within the polymeric, or conjugated longer forms.

To effect the foregoing the gas discharge tube is generally enclosed in an elongate reflective housing defined by a cylindrical end in which the anode of the tube is retained and a generally parabolic mirror adjacent the cathode terminal. A voltage multiplier connected across the cathode and anode terminals is then driven to the discharge potential of the tube, resulting in the characteristic emissions of the tube gases. This potential is cycled at the pulse durations of a voltage controlled oscillator rectified to produce swinging between saturation limits, which can be varied by the voltage setting of a potentiometer.

DESCRIPTION OF THE PREFERRED EMBODIMENT

Figure 1:
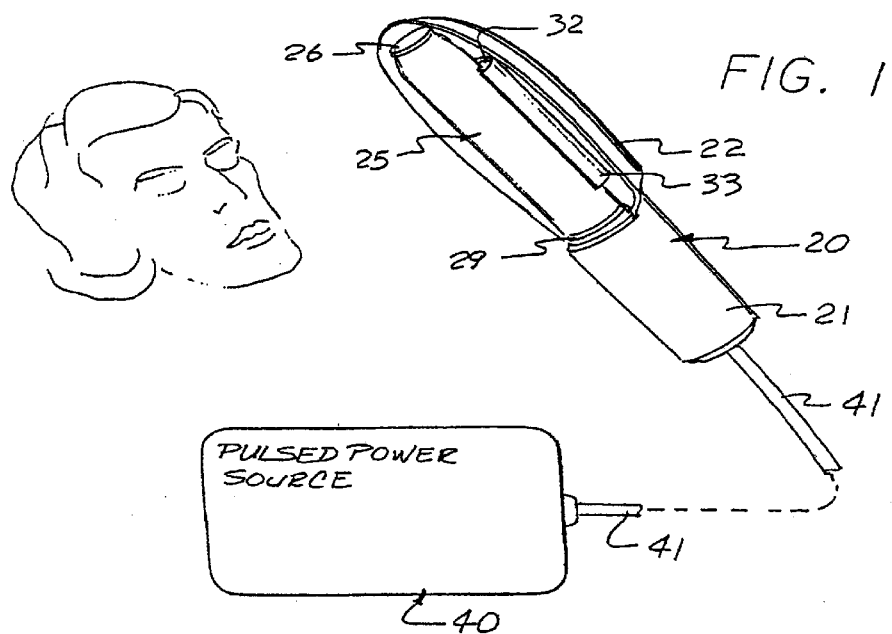
FIG. 1 is a diagrammatic illustration of the inventive irradiation system deployed adjacent a person.
Figure 5:
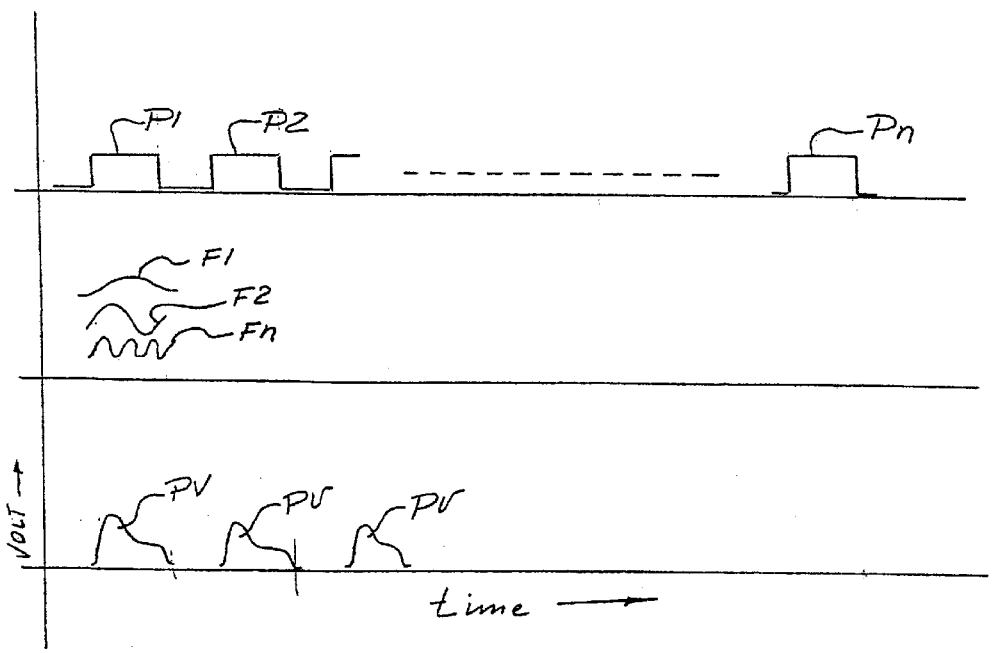
FIG. 5 is a graphical illustration of a pulse train of electrical ionization levels applied to said plasma tube.
Figure 2:
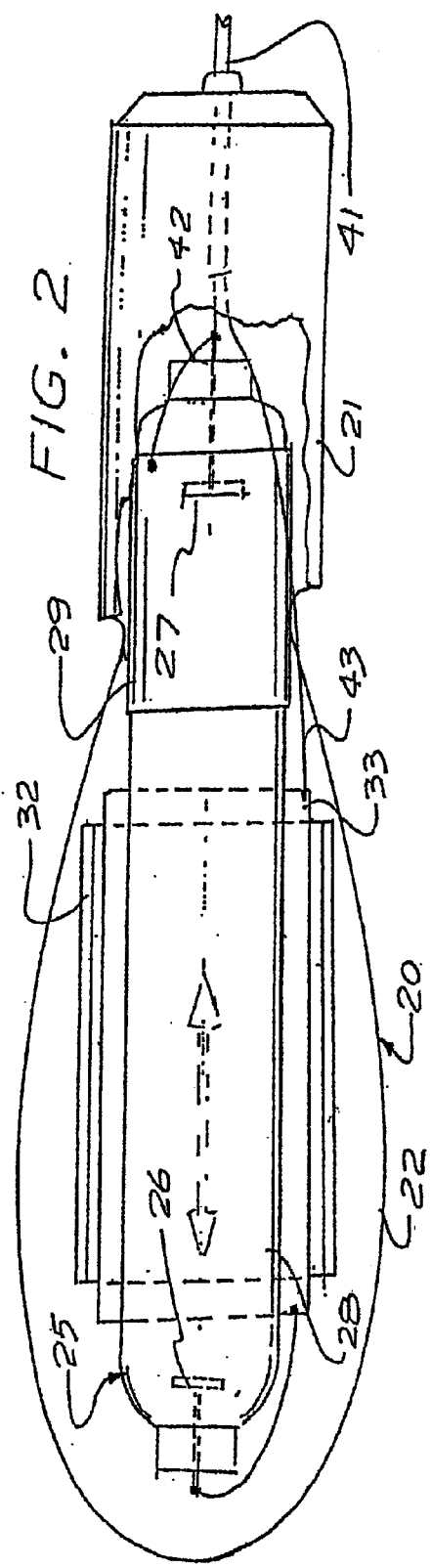
FIG. 2 is a top view of an inventive plasma tube useful with the instant irradiation system.
Figure 3:
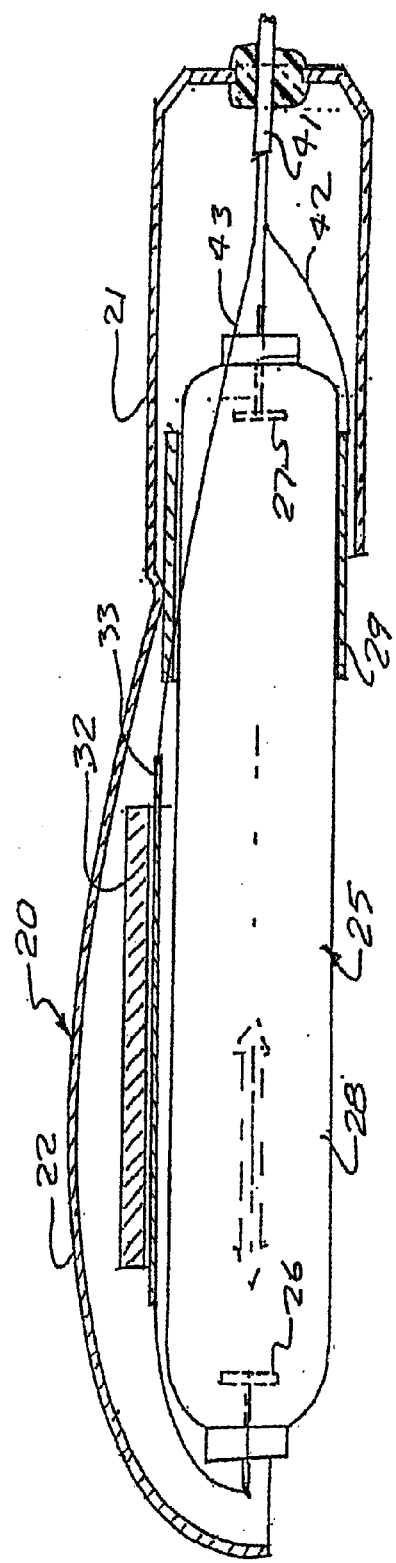
FIG. 3 is a side view of the plasma tube shown in FIG. 2.
Figure 4:
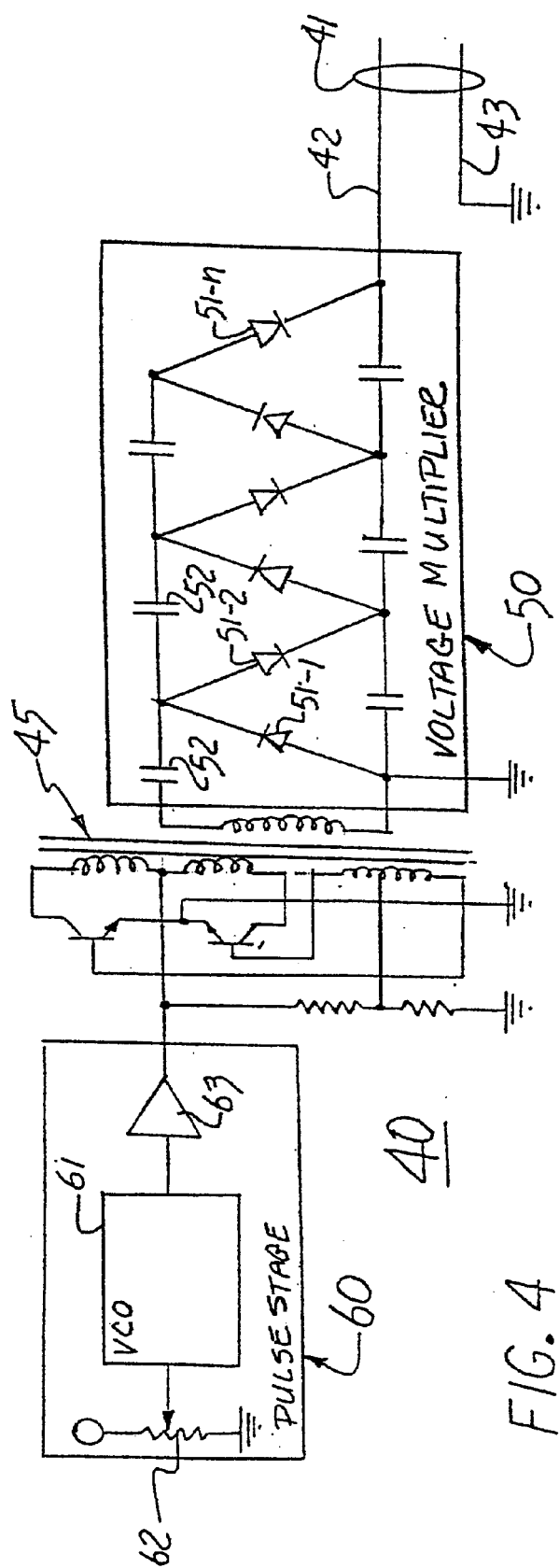
FIG. 4 is a circuit diagram of a pulsed power circuit useful in exciting the plasma tube.

As shown in FIGS. 1 through 5, the inventive system, generally designated by the numeral 10, includes a plasma tube assembly 20 connected by a power cord 41 to a power source 40. Preferably the plasma tube assembly is conformed as a hand held device, characterized by a handle 21 extending from a reflecting shield 22 to form a common interior. Received within the common interior is a plasma tube 25 provided with cathode 26 in the tube end located subjacent the reflecting shield 22, and an anode 27 within the handle 21. Tube 25 includes is defined by a tubular glass wall or enclosure 28 through the ends of which the cathode 26 and anode 27 project into the interior. The anode end, received within the handle 21, includes a cylindrical shield 29 of a conducting material like copper surrounding the anode 27 and the adjacent plasma region.

At the other tube end, subjacent the reflecting shield 22, a magnetic piece 32 is inserted along the tube wall, overlying the high discharge region adjacent the cathode 26, with the north—south magnetic field aligned orthogonal to the plasma beam PB. A further conductive shielding sheet 33, in the form of an aluminium foil segment, is placed between the magnetic piece 32 and the tube surface. The shields 29 and 33 are then connected to the positive output lead 42 and the negative lead 43 forming the power cord 41 of the power supply 40, leads 42 and 43 also connecting and to anode 27 and cathode 26.

Tube 25 contains a group of gases of the following mix:
H2O=66%
CO2=24%
N2=3%
H2CO3=3% in percentages by weight, held to +/−5%. Of course, these gases are at extremely low pressures in order to allow for ionization once sufficient electrical potential is applied across the electrodes. Upon ionization each of the gases emits its characteristic spectrum of light frequencies associated with the transitions in the electron orbitals. This light spectrum is particularly intense along that portion of the plasma beam PB next to the cathode 26 and subjacent the reflecting foil sheet 33. It is this same portion of the beam PB that is also exposed to the bending effects of the magnetic piece 32, further enhancing the emission levels in a direction opposite to the reflector 22.

It is to be noted that the spectral signature of the gases N2. CO2 and H2O, i.e., molecular nitrogen, carbon dioxide and water, define the spectral background of virtually all biological matter. Superposed thereon will be the spectral signature of H2CO3, one of the simplest molecular combinations of a carbon compound, which again subsists in virtually all protein or amino acid chains. This superposition of emitted spectra is then useful to irradiate adjacent tissue TI exciting selected electron orbitals in the tissue to a higher state.

The foregoing mechanism has the effect of increasing the chemical reactivity concurrent with an increase in polarization potential of those molecular segments that are polarized. Thus by absorbing the emitted spectra the potential across a cell wall is increased as is the electrical charge on either side thereof. This then enhances the transfer of electrical charge to the cell interior which occurs in the frequency domain of the 'wet' circuit.

To insure that the foregoing effects are at the cell wet circuit frequency bandpass, the power supply circuit 40 includes a pulse stage 60 gated by a voltage controlled oscillator 61 set in its oscillation frequency of about 65 Hertz by potentiometer 62 connected between a positive signal E+ and ground. The wiper of potentiometer 62 then sets the oscillation frequency of the oscillator 61, the output thereof being connected to the input of an operational amplifier 63 driven between its saturation limits. In this manner a series of positive and negative pulses P+ and P− is produced at the output of amplifier 63, each of an amplitude determined by the saturation limit and of a duration set by the oscillation cycle. This signal is then amplified by a power amplifier 65 and thereafter fed to the primary of a transformer 45. The secondary, in turn, is connected to a multi-stage voltage doubler or multiplier generally at 50, formed by way of a lattice of diodes 51-1 through 51-n interconnected by capacitors 52. The last diode stage 51-n then connects to the positive lead 42 of the power cord 41 while the ground is connected to the other lead 43.

It is to be noted that once the electrical potential across the cathode 26 and anode 27 exceeds the breakdown potential of the tube ionization will occur along with the associated reduction in impedance. This breakdown entails a frequency bandpass that is determined by the capacitors 52 together with the filtering components of a shaping network 55, which together set the pass range to include the frequencies of the cell wet circuit. In this manner resonance with the cell electrical functions can be achieved to further enhance the effect of the light spectra emitted by the plasma bursts.

Thus, for example, a pulse train P1–Pn emitted at the output of amplifier 65 excites during each pulse a group of frequencies F1–Fn, which once superposed describe the signal shape PV across the tube electrodes in the course of ionization breakdown. The signal PV oscillations then are expressed as variations in emission intensity since for all practical purposes the emission spectra are so far removed that no coupling is possible. Thus by allowing a relatively wide range of frequencies F1–Fn, i.e., the intensity of the plasma signal PV will be modulated within the frequency range of a cell wet circuit. To preclude emissions in the ultraviolet (280 nanometer) range the material structure of the tube wall 28 may comprise borosilicate rather than ordinary glass or quartz.

Obviously, many modifications and variations can be accomplished without departing from the spirit of the above teachings. It is therefore intended that the scope of the instant invention be determined solely by the claims appended hereto.

I claim:

1. Apparatus for illuminating biological matter with preselected frequency spectra, comprising:
   - a vacuum tube of a generally elongate form defined by a cylindrical exterior wall made of translucent material;
   - an anode formed in one end of tube;
   - a cathode formed in the other end of said tube;
   - a tubular conductive shield formed around a first portion of said tube adjacent said anode, said tubular shield being electrically connected to said anode;
   - a reflective surface mounted proximate a second portion of said tube adjacent said cathode, said reflective surface comprising conductive material electrically connected to said cathode;
   - a magnetic piece of a generally planar configuration aligned along said reflective surface distal of said second portion of said tube, said magnetic piece being transversely magnetized along a magnetic direction generally orthogonal to said tube;
   - an enclosure including a handle conformed to receive said first portion of said tube together with said tubular shield, and a reflector extending from said handle over said second portion of said tube together with said reflective surface and said magnetic piece;
   - a source of electrical excitation connected between said anode and said cathode, said source including pulsing means for modulating said electrical excitation in a frequency domain of electrochemical reactions of said biological matter; and gases in said tube of molecular combinations of
   $H2O=66\%$
   $CO2=24\%$
   $N2=3\%$
   $H2CO3=3\%$
   +/−5%, by weight.

2. Apparatus according to claim 1, wherein:
   said source of electrical excitation includes a voltage multiplier defined by a series of diodes bridged by capacitors; and
   said tube is formed of borosilicate.

3. Apparatus for illuminating biological matter with preselected electromagnetic frequency spectra, comprising:
   - a translucent vacuum tube of a generally elongate form defined by a cylindrical exterior wall made of glass and including water vapor, carbon dioxide, molecular nitrogen and a carbonic acid in gaseous form in the interior thereof;
   - an anode formed in one end of said tube and a cathode formed in the other end of said tube;
   - a tubular conductive shield formed around a first portion of said tube adjacent said anode, said tubular shield being electrically connected to said anode;
   - a reflective surface mounted proximate a second portion of said tube adjacent said cathode, said reflective surface comprising conductive material electrically connected to said cathode;
   - a magnetic piece of a generally planar configuration aligned along said reflective surface distal of said second portion of said tube, said magnetic piece being transversely magnetized along a magnetic direction generally orthogonal to said tube; and
   - an enclosure including a handle conformed to receive said first portion of said tube together with said tubular shield, and a reflector extending from said handle over said second portion of said tube together with said reflective surface and said magnetic piece.

4. Apparatus according to claim 3, wherein:
   said gaseous water vapor, carbon dioxide, molecular nitrogen and carbonic acid are contained in said tube at the following chemical composition and weight ratio:
   $H2O=66\%$
   $CO2=24\%$
   $N2=3\%$
   $H2CO3=3\%$
   +/−5%, by weight.

5. Apparatus according to claim 4, further comprising:
   a source of electrical excitation connected between said anode and said cathode, said source including pulsing means for modulating said electrical excitation in a frequency domain of electrochemical reactions of said biological matter.

6. Apparatus according to claim 5, wherein:
   said source of electrical excitation includes a voltage multiplier defined by a series of diodes bridged by capacitors.

\* \* \* \* \*